US006697451B2

United States Patent
Acharya et al.

(10) Patent No.: US 6,697,451 B2
(45) Date of Patent: Feb. 24, 2004

(54) DYNAMIC PHANTOM AND METHOD FOR EVALUATING CALCIUM SCORING

(75) Inventors: Kishore C. Acharya, Brookfield, WI (US); Marcela A. Gonzalez, Milwaukee, WI (US); Gary J. Walloch, Milwaukee, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/946,288

(22) Filed: Sep. 5, 2001

(65) Prior Publication Data

US 2003/0048867 A1 Mar. 13, 2003

(51) Int. Cl.$^7$ ................................................ A61B 6/00
(52) U.S. Cl. ................................ 378/18; 378/4; 378/8; 378/69; 378/95; 378/115; 600/425; 600/427; 250/363.04
(58) Field of Search .......................... 378/18, 8, 4, 69, 378/95, 115; 600/425, 427, 428, 413, 420; 250/363.04

(56) References Cited

U.S. PATENT DOCUMENTS

| | | | | |
|---|---|---|---|---|
| 4,182,311 A | * | 1/1980 | Seppi et al. | 600/428 |
| 4,646,334 A | | 2/1987 | Zerhouni | |
| 4,837,686 A | | 6/1989 | Sones et al. | |
| 4,870,666 A | * | 9/1989 | Lonn | 378/18 |
| 4,873,707 A | | 10/1989 | Robertson | |
| 4,985,906 A | * | 1/1991 | Arnold | 378/18 |
| 5,034,969 A | | 7/1991 | Ozaki | |
| 5,335,260 A | * | 8/1994 | Arnold | 378/207 |
| 6,154,516 A | * | 11/2000 | Heuscher et al. | 378/15 |
| 6,224,257 B1 | | 5/2001 | Launay et al. | |
| 6,233,304 B1 | * | 5/2001 | Hu et al. | 378/8 |
| 6,314,313 B1 | | 11/2001 | Romeas et al. | |
| 6,421,552 B1 | * | 7/2002 | Hsieh | 600/425 |

FOREIGN PATENT DOCUMENTS

| | | |
|---|---|---|
| EP | 1 016 376 A2 | 7/2000 |
| EP | 1 092 392 A2 | 4/2001 |
| WO | WO 00/33252 | 6/2000 |

OTHER PUBLICATIONS

"Catphan®"; 32–page brochure; Product of The Phantom Laboratory.
"Liqui–Phil™ Phantoms"; 8–page brochure; Product of The Phantom Laboratory.
"Magphan®"; 24–page brochure; Product of The Phantom Laboratory.
"Quantification of Coronary Artery Calcium Using Ultrafast Computed Tomography"; Agatston et al.; Journal of the American College of Cardiology, vol. 15, No. 4, pp. 827–832 (Mar. 15, 1990).
"R S V P Pelvis™"; 6–page brochure, Product of The Phantom Laboratory.
"R S V P Phantom™ Radiosurgery Verification Phantom"; 8–page brochure; Product of The Phantom Laboratory.

(List continued on next page.)

Primary Examiner—Robert H. Kim
Assistant Examiner—George Wang
(74) Attorney, Agent, or Firm—Foley & Larder; Peter J. Vogel; Michael A. Della Penna

(57) ABSTRACT

A method of evaluating a substance scoring system comprises acquiring data from a phantom using an imaging system, moving at least a portion of the phantom during the acquiring step, and generating an actual substance score for the phantom based on the data acquired using the imaging system. The phantom simulates a human organ such as a human heart. The phantom is provided with a motion profile that simulates a motion profile of the human organ.

21 Claims, 10 Drawing Sheets

OTHER PUBLICATIONS

"Sectional Phantoms"; 8–page brochure; Product of The Phantom Laboratory.

"The Phantom Patient™"; 8–page brochure; Product of The Phantom Laboratory.

"The RANDO® Phantom"; 8–page brochure; Product of The Phantom Laboratory.

"Welcome to The Phantom Laboratory"; 28–page brochure; Product of The Phantom Laboratory.

"Three–Dimensional Biomedical Imaging", Richard A. Robb, Ph.D., vol. I, Chapter 5, pp. 139–146; CRC Press, Inc. (1985).

"Development and Assessment of Real Cardiac Motion Simulation Phantom"; Article [in Japanese]; Kimura F. et al.; Nippon Acta Radiologica; 61(1):29–32 (Jan. 2001).

"Vascular Surgery" ('Saphenous Vein Harvesting', 'Saphenous Vein Harvesting—Balloon', 'Heart Surgery'); 3–pg. document; [obtained from Internet www.limbsandthings.com/surgpg7.htm]; [Page last updated: Jun. 19, 2001].

"Vascular Surgery" ('Saphenous Leg for Vein Harvesting', 'Saphenous Vein Balloon Harvesting Trainer', 'Pulsatile Heart and Pump') 3–pg. document; [obtained from Internet www.limbsandthings.com/vascular.htm]; [Page last updated: Jun. 19, 2001].

"Study of Cardiac Ejection Fraction and Volume Measurements Using a Dynamic Cardiac Phantom and SPECT"; S. Jang et al.; vol. 3, pp. 1581–1585; In the Conference Record of the IEEE Nuclear Science Symposium & Medical Imaging Conference in San Francisco, CA, held Oct. 31–Nov. 6, 1993, by the IEEE.

"Evaluation of Ejection Fraction Measurements in Gated Cardiac Imaging Using Dynamic Cardiac Phantoms"; S. Jang et al.; vol. 4, pp. 1735–1738; In the Conference Record of the IEEE Nuclear Science Symposium & Medical Imaging Conference in Norfolk, VA, held Oct. 30–Nov. 5, 1994, by the IEEE.

"Cardiac Ejection Fraction and Volume Measurements Using Dynamic Cardiac Phantoms and Radionuclide Imaging"; S. Jang et al.; vol. 41, No. 6, pp. 2845–2849; Dec. 1994; IEEE Transactions on Nuclear Science.

Lynn S. Broderick et al.; "Measurement of Coronary Artery Calcium with Dual–Slice Helical CT Compared with Coronary Angiography: Evaluation of CT Scoring Methods, Interobserver Variations, and Reproducibility"; AJR:167; Aug. 1996; pp. 439–444.

Hyo–Chun Yoon, MD, PhD., et al.; "Coronary Artery Calcium: Alternate Methods for Accurate and Reproducible Quantitation"; AUR; Oct. 1997; vol. 4, No. 10; pp. 666–673.

Yuji Ukai et al.; "A Coronary Calcification Diagnosis System Based on Helical CT Images"; IEEE; 1998; pp. 1208–1212.

Wilson et al.; "Automated Detection of Microcalcifications in Mammograms through Application of Image Pixel Remapping and Statistical Filter"; Eleventh IEEE Symposium on Computer–Based Medical Systems; pp. 270–274.

Okhashi et al.; "Application of a Neural Network to Automatic Gray–level Adjustment for Medical Images"; IEEE vol. 2 of 3; Nov. 1991; pp. 974–980.

* cited by examiner

| GROUP NUMBER | ALGORITHM RANGE | TARGET CT NUMBER AT 120 KV | GROUP ANGLE (IN DEGREES) |
|---|---|---|---|
| 1 | – | 0 HU | 0 |
| 2 | 0–129 HU | 110 HU | 45 |
| 3 | 130–199 HU | 150 HU | 135 |
| 4 | 200–299 HU | 250 HU | 180 |
| 5 | 300–399 HU | 350 HU | 225 |
| 6 | 400+ HU | 450 HU | 315 |
FIG. 5
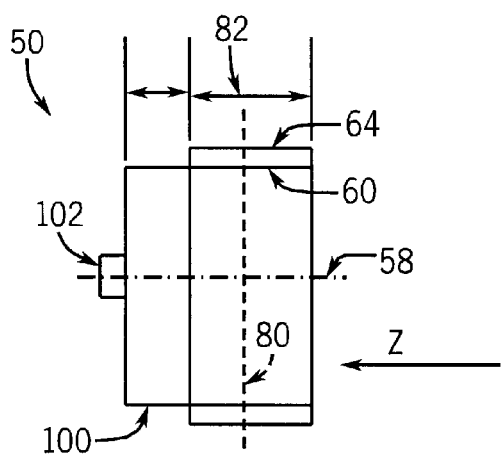
FIG. 6
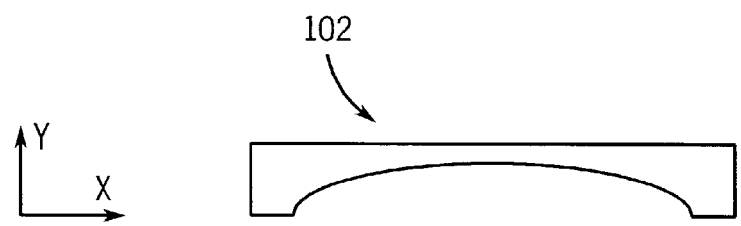
FIG. 7

US 6,697,451 B2

DYNAMIC PHANTOM AND METHOD FOR EVALUATING CALCIUM SCORING

FIELD OF THE INVENTION

This invention relates generally to imaging systems and, more particularly, to a phantom for use in evaluating substance scoring using imaging system-generated images.

BACKGROUND OF THE INVENTION

Imaging systems include a source that emits signals (including but not limited to x-ray, radio frequency, or sonar signals), and the signals are directed toward an object to be imaged. The emitted signals and the interposed object interact to produce a response that is received by one or more detectors. The imaging system then processes the detected response signals to generate an image of the object.

For example, in computed tomography (CT) imaging, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third-generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two-dimensional slice taken through the object.

One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. Such a system generates a single helix from a one-fan-beam helical scan. To further scan time, multi-slice helical scans can also be used. The helix mapped out by the fan beam yields projection data from which images in each prescribed slice may be reconstructed. In addition to reduced scanning time, helical scanning provides other advantages such as imaging at any location, reduced dose, and better control of contrast.

It is known to use imaging data to identify evidence of certain diseases by detecting and quantifying, i.e., "scoring", substances that may be present in a patient's system. One known software system, for example, analyzes CT images of the heart to quantify amounts of calcium in coronary regions of interest. Scoring is based upon the volume and Hounsfield unit of a calcified region. A number called the "calcium score" expresses the quantity of calcium present in the patient's arterial system.

It would be desirable to provide a system and method for verifying accuracy of substance-scoring systems. It also would be desirable to provide a system and method for measuring the validity, reproducibility and repeatability of a substance score for different imaging systems (e.g. CT single-slice or multi-slice), for different scanning methods (e.g. CT helical or axial), and for different image reconstruction algorithms.

Co-pending application Ser. No. 09/541,147, filed Mar. 31, 2000, discloses a preferred phantom which simulates a heart with calcium deposits and related method that are usable in this manner. It is possible to use the phantom described Ser. No. 09/541,147 as either a static (non-moving) or dynamic (moving) phantom, inasmuch as disclosed phantom is robust and can be used either way. Dynamic phantoms are desirable because a human heart continues pumping during imaging operations, and therefore a dynamic phantom provides a better simulation of the human heart. Therefore, it would be desirable to provide a phantom and method in which the phantom is capable of moving, especially a phantom and method in which the phantom is capable of moving in a manner that simulates pumping of a human heart.

BRIEF SUMMARY OF THE INVENTION

According to a first preferred aspect, a method of evaluating a substance scoring system comprises acquiring data from a phantom using an imaging system, moving at least a portion of the phantom during the acquiring step, and generating an actual substance score for the phantom based on the data acquired using the imaging system. The phantom simulates a human organ such as a human heart. The phantom is provided with a motion profile that simulates a motion profile of the human organ.

According to a second preferred aspect, a system comprises a phantom, a movable phantom holder, and an imaging system. The phantom includes a core and a plurality of volumes embedded in the core. Each of the plurality of volumes has an imaging number that simulates a substance of interest, with different ones of the plurality of volumes having different imaging numbers that simulate different concentrations of the substance. The phantom is mounted to the movable phantom holder, which causes the phantom to move. The imaging system generates an actual substance score, which expresses a quantity and a concentration of the simulated substance present in the phantom.

The above-described phantom and method allow a scoring system user to verify substance scoring accuracy and to compare scores resulting from different imaging systems, scanning methods and reconstruction algorithms during motion of the simulated organ.

BRIEF DESCRIPTION OF THE DRAWINGS

FIG. 5 is a table of CT number ranges and corresponding group target CT numbers and positional angles for one embodiment of the phantom shown in FIG. 3;

FIG. 6 is a side view of the phantom shown in FIG. 3;

FIG. 7 is a diagram of a mounting bracket for the phantom shown in FIG. 3;

FIG. 2B is an example of a specific implementation of the circuit of FIG. 12A;

DETAILED DESCRIPTION OF THE INVENTION

Figure 1:
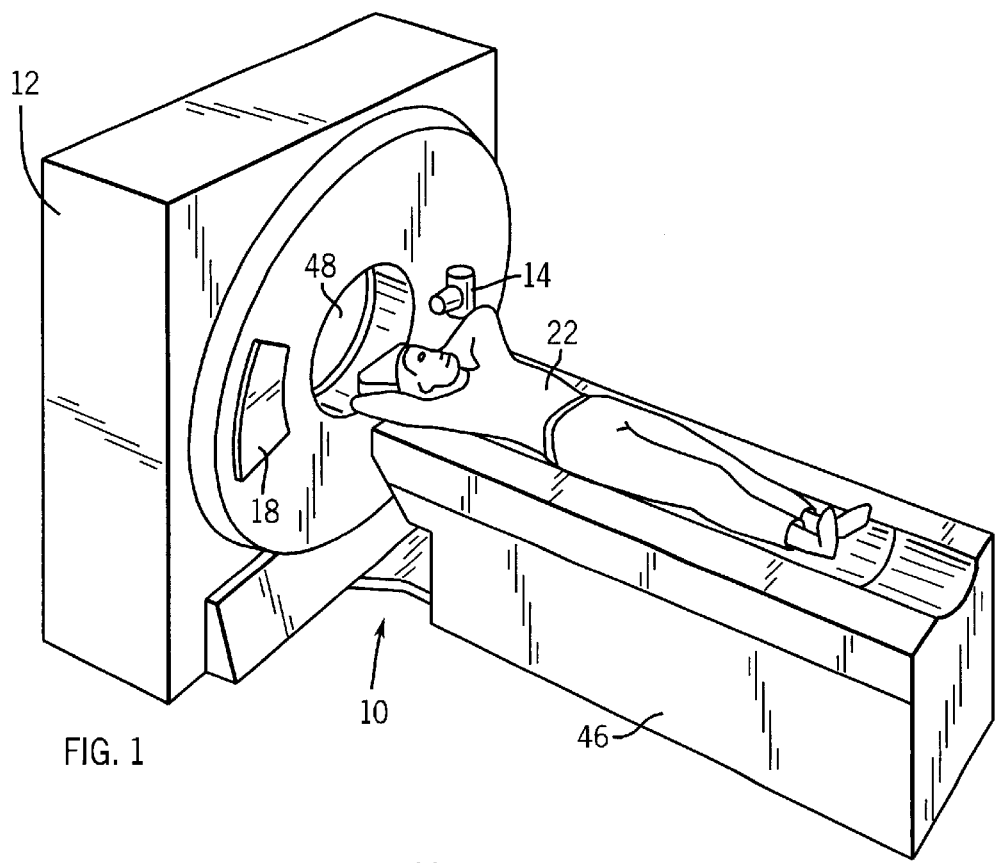
FIG. 1 is a pictorial view of a CT imaging system.
Figure 2:
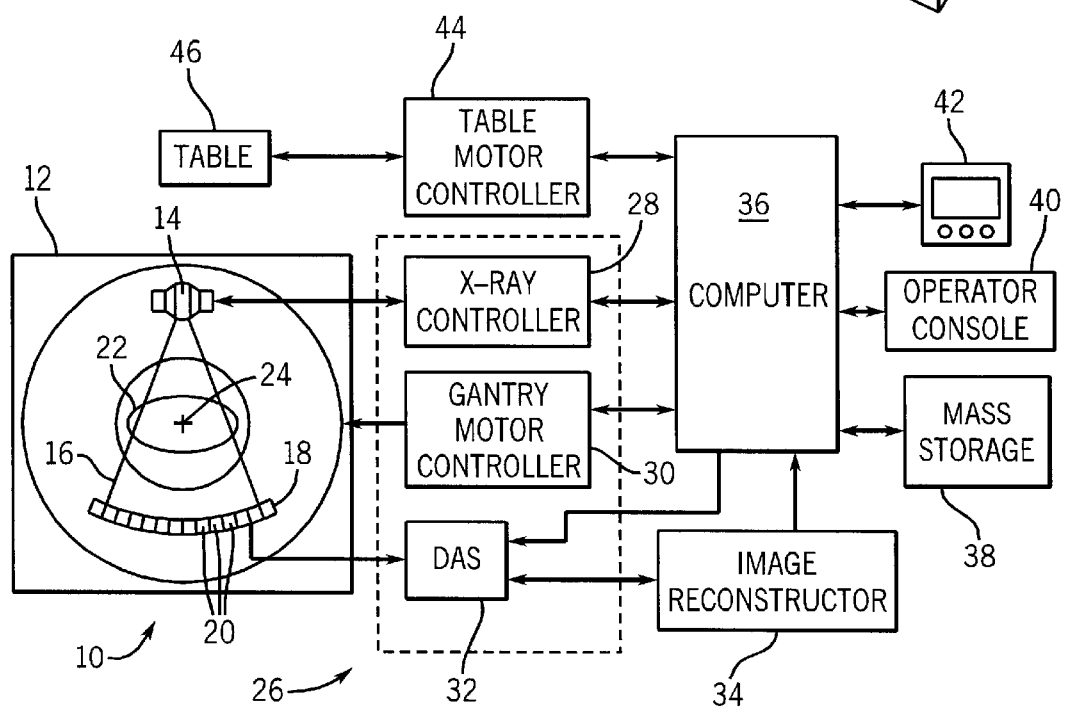
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. X-ray beam 16 is collimated by a collimator (not shown) to lie within an X-Y plane of a Cartesian coordinate system and generally referred to as an "imaging plane". Detector array 18 is formed by detector elements 20 which together sense the projected x-rays that pass through an object 22 such as a medical patient. Detector array 20 may be a single-slice detector or a multi-slice detector. Each detector element 20 produces an electrical signal that represents the intensity of an impinging x-ray beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 along a Z-axis through gantry opening 48.

Figure 3:
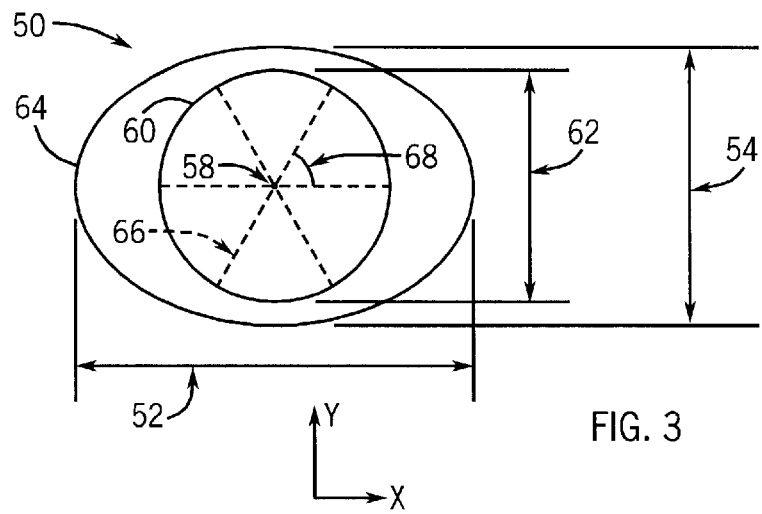
FIG. 3 is a frontal view of a phantom for calcium scoring.

In one embodiment and referring to FIG. 3, a phantom 50 for use in calcium scoring simulates regions of the human coronary system. As shown frontally in FIG. 3, e.g. in an X-Y plane, phantom 50 is oval in shape, having, for example, a long axis 52 of 35 centimeters and a short axis 54 of 25 centimeters. Phantom 50 includes a cylindrical core 60 representing the heart and having a diameter 62, for example, of 20 centimeters. Core 60 is made of a material having an imaging number (i.e., a CT number in the case of the CT imaging system 10) simulating that of heart muscle, for example, a plastic material having a CT number of 60 Hounsfield units at a source 14 voltage of 120 kilovolts.

Core 60 is located, e.g. centered, inside an elliptical ring 64 representing tissues surrounding the heart. Ring 64 is made of a material having a CT number simulating that of heart tissue, for example, a plastic material having a CT number of 60 Hounsfield units at a source 14 voltage of 120 kilovolts. As shall be described below, a plurality of rods (not shown in FIG. 3) are embedded in core 60 along lines 66 radiating from a phantom axis 58 (shown in FIG. 3 as coming out of the page, i.e., orthogonal to the X-Y plane shown in FIG. 3). Radial lines 66 extend at angles 68 from phantom axis 58.

Figure 4:
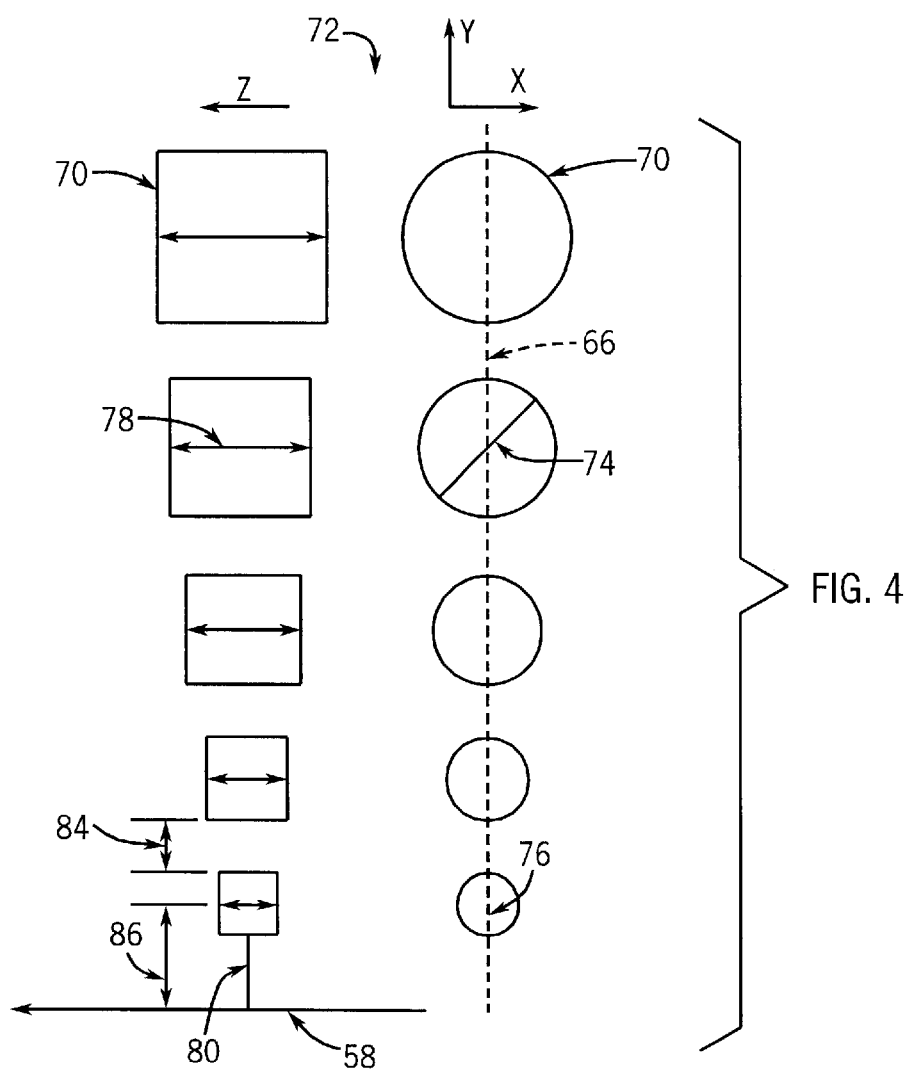
FIG. 4 is a diagram of shape and orientation for rods included in the phantom shown in FIG. 3.

As shown in FIG. 4, phantom 50 includes a plurality of volumes 70, e.g. rods, simulating a plurality of calcified coronary regions. Rods 70 differ from one another in length, diameter and density. Each rod 70 simulates, in dimensions and densities, a calcified material typically found in patient coronary systems. More particularly and in one embodiment, thirty rods 70 are embedded in core 60 in six groups 72 of five rods 70 each. Each group 72 is arranged along a radial line 66 and has a target CT number (not shown in FIG. 4) as shall be described below. Rods 70 in each group 72 are separated from one another by a distance 84 of, for example, four millimeters and have diameters 74 of 2, 3, 4, 5 and 6 millimeters respectively, with diameters 74 increasing with distance from phantom axis 58. Center 76 of smallest rod 70 in a group 72 is located, for example, a distance 86 of five millimeters from phantom axis 58 along the appropriate radial line 66. Each rod 70 has, for example, a length 78 equal to its diameter 74 and is aligned lengthwise parallel to phantom axis 58. All rods 70 are lengthwise-centered on a midplane 80 which bisects phantom 50.

In the currently preferred embodiment, the phantom 50 further includes additional reference rods (not shown) used for calibration. The reference rods have a diameter of 15 millimeters and are placed further out along the radial lines 66 than the remaining rods 70. The 15 millimeter diameter of the reference rods ensures that all of the x-ray beam 16 passes through the reference rods, thereby avoiding errors due to the partial volume effect during calibration.

Each group 72 is made of a material having a CT number representative of a range of calcium concentrations as reflected in CT images through the CT number. CT numbers (and materials having such numbers) are selected for rods 70 based on, for example, a scoring algorithm used by a calcium scoring system with which phantom 50 is to be used. One such algorithm categorizes calcification according to CT number in calcium concentration ranges 90 as shown in FIG. 5. For a 120 kilovolt source 14 voltage, ranges 90 include, for example, zero to 129 Hounsfield units, 130 to 199 Hounsfield units, 200 to 299 Hounsfield units, 300 to 399 Hounsfield units, and above and including 400 Hounsfield units. With one exception as shall be described below, a target CT number 92 is selected for each group 72 from the middle of the corresponding range 90. A middle value is selected to prevent range 90 boundary crossing when system 10 is subjected to noise. An exception is a calibration group 94 that is used to verify imaging system 10 accuracy.

Calibration group 94 has a target CT number 92 of zero while other groups 72 have target CT numbers 92 of, e.g. 110, 150, 250, 350 and 450 Hounsfield units respectively. To achieve these Hounsfield values, the rods 70 are constructed of plastic having a density in the range of about 1.2–1.3 g/cc (i.e., with different densities corresponding to different concentrations of calcium), for example, as available from The Phantom Laboratory, P. O. Box 511, Salem, N.Y. 12865-0511 (www.phantomlab.com). Phantom 50 is fabricated such that actual target CT numbers 92 are within tolerances of +5 HU and −5 HU of nominal target CT numbers 92. Thus nominal CT numbers are closely approximated without engendering fabrication difficulty. Groups 72 are positioned along radial lines 66, for example, at angles 68 as shown in FIG. 5, i.e., at 0 degrees, 45 degrees, 135 degrees, 180 degrees, 225 degrees, and 315 degrees respectively.

As shown in FIG. 6, core 60 and ring 64 are cylindrical in shape along phantom axis 58 and have a length 82 of, e.g., five centimeters. Core 60 has an alignment region 100 extending, for example, three centimeters in the direction of phantom axis 58. Phantom 50 includes a mounting bracket 102, removably affixed to alignment region 100 and shown frontally in FIG. 7. Phantom 50 is supported during imaging by a phantom holder (not shown), to which mounting bracket 102 is removably affixed.

In use, phantom 50 and the supporting phantom holder are placed on table 46. A centroid of phantom 50 is calculated and, based on the calculated centroid, phantom 50 is aligned using laser light to align the phantom 50 visually as is typically done with a human patient. Rods 70 are aligned along the imaging system 10 Z-axis.

When phantom 50 is placed on table 46 and aligned for imaging in imaging system 10, it simulates, for example, calcified coronary arterial regions of interest to the user of a calcium scoring system. The user then generates imaging system 10 images of the simulated calcified regions, calcium-scores the images, and compares results of the calcium scoring to expected phantom-image results.

The above-described phantom allows a user of a calcium scoring system to evaluate scoring system accuracy. The user also can evaluate different imaging systems (e.g. single-slice CT or multi-slice CT), different scanning methods (e.g. helical or axial), and different reconstruction algorithms relative to the calcium scoring system and thereby determine whether a calcium score is valid, reproducible and repeatable.

Figure 8:
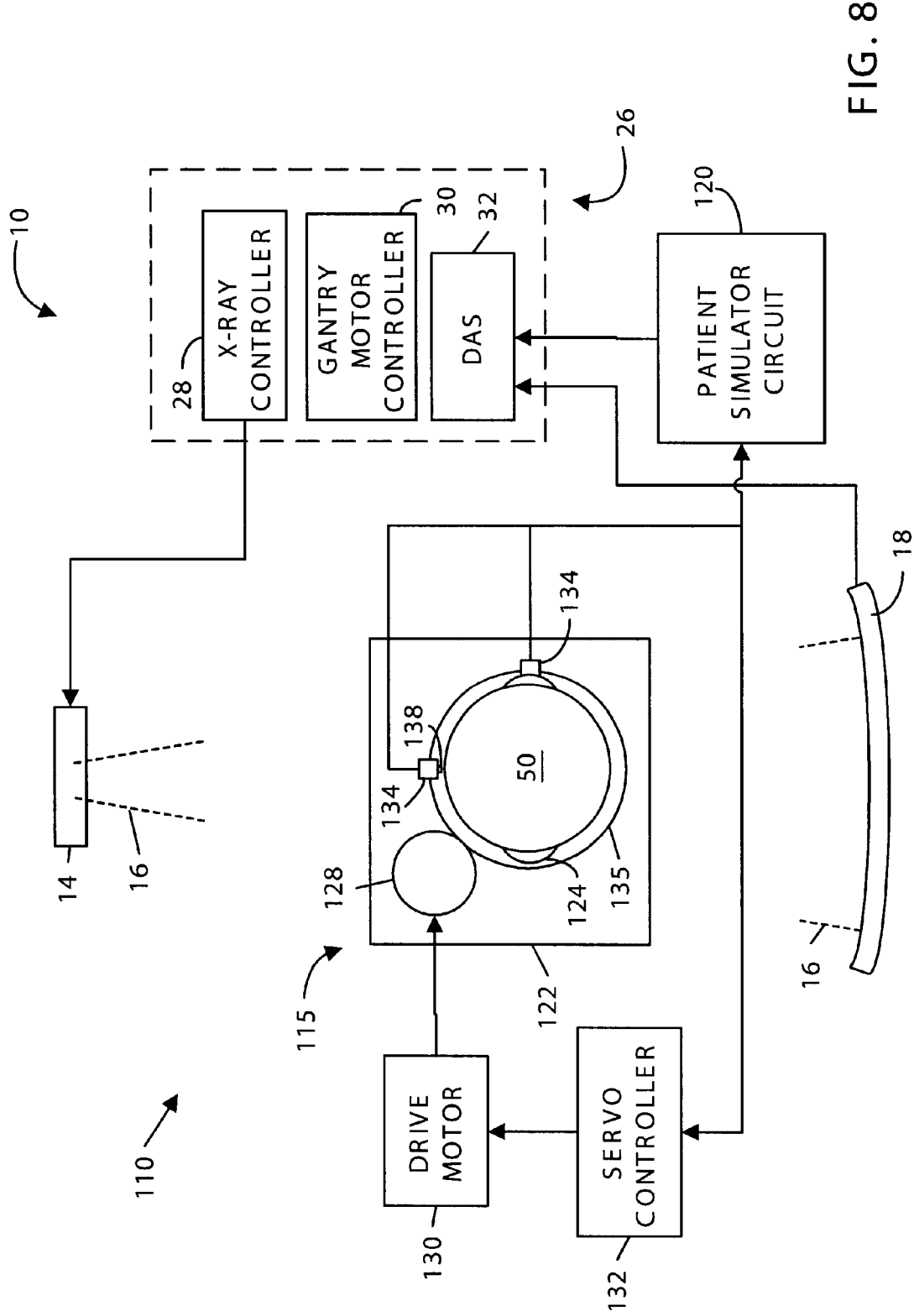
FIG. 8 is a block diagram of a system that incorporates the phantom of FIG. 3.
Figure 9:
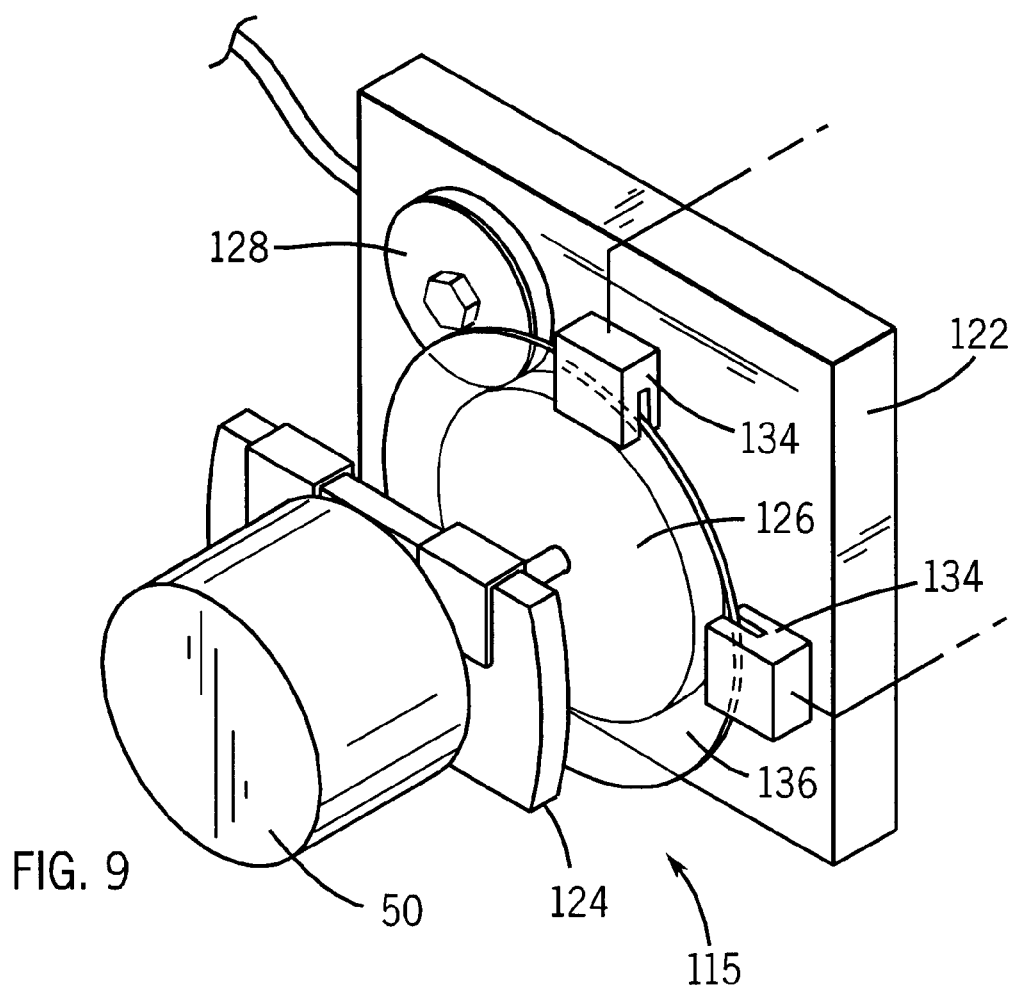
FIG. 9 shows a phantom holder assembly of FIG. 8 in greater detail.

In another embodiment and referring now to FIGS. 8–9, the phantom 50 is used in connection with a calcium scoring evaluation system 110 having a phantom holder assembly 115 that drives movement of the phantom 50. This permits pumping motion of a human heart (or other dynamic organ) to be simulated and thereby permits a more accurate simulation of the human heart to be achieved during scoring system evaluation. FIG. 8 is a block diagram of the evaluation system 110 that incorporates the phantom 50 of FIG. 3. FIG. 9 shows a phantom holder assembly 115 of FIG. 8 in greater detail.

The evaluation system 110 comprises the CT imaging system 10, the phantom 50, the phantom holder assembly 115, and a patient simulator circuit 120. The CT imaging system 10 is the same as described in connection with FIG. 1, although only a portion of the CT imaging system 10 is shown. Also, in FIG. 8, it should be noted that the CT imaging system 10 is not drawn to scale relative to the remainder of the CT scoring evaluation system 110.

The phantom 50 is mounted to the phantom holder assembly 115, which is positioned relative to the CT system 10 in such a way (e.g., within the gantry 12 on the patient table 46) so as to simulate placement of a human heart during an imaging operation of the human heart. The phantom holder assembly 115 comprises a support member 122, a phantom holder bracket 124, a disk 126, a drive wheel 128, a drive motor 130, a programmable servo controller 132, and a pair of switches 134.

The phantom holder bracket 124 receives the bracket 102 of the phantom 50 so as to removably affix the phantom 50 to the phantom holder assembly 115. The bracket 124 is mounted to the disk 126 which in turn is mounted to the support member 122 by way of a shaft (not shown). The support member 122 serves as a mechanical mount for the bracket 124 and the disk 126, as well as the remaining components 128–134 of the phantom holder assembly 115. The disk 126 is in contact with the drive wheel 128, thereby permitting the drive wheel 128 to drive movement of the disk 126 by force of friction. To this end, the perimeter of the drive wheel 128 may provided with a rubber surface or other suitable material to promote torque transfer from the drive wheel 128 to the disk 126.

The drive wheel 128 is driven by the servo motor 130. Although in FIG. 8 the drive motor 130 is depicted as being separate from the support member 122, it is seen in FIG. 9 that the drive motor 130 is in fact mounted on an opposite side of the support member 122 relative to the drive wheel 128. In practice, a motor shaft (not illustrated) extends through the support member 122 to drive the drive wheel 128.

The drive motor 130 is controlled by the servo controller 132. The servo controller 132 controls the drive motor 130 to provide the phantom 50 with a reciprocating motion, thereby causing the phantom 50 to move in and out of a scanning plane of the CT system 10. The motion profile may simply be periodic (e.g., sinusoidal) or, preferably, may simulate the motion profile of a human heart. In other words, the phantom 50 preferably moves at a rate that corresponds to the rate of expansion/contraction of a human heart. In this case, the speed of rotation can be programmed in accordance with the duration and slopes of the various deflections in the EKG signals (P-wave, QRS-wave and T-wave). In either case, the motion profile is programmed into the servo controller 132 which controls the drive motor 130.

The servo controller 132 receives position feedback from the switches 128. In practice, the switches 128 are preferably optocoupler switches, and an additional disk 136 (see FIG. 9) is mounted to the disk 126. The disk 136 is generally transparent except for a pair of opaque regions 138. The opaque regions 138 pass through the optical switches 134 to serve as limit switches for position feedback. That is, as the phantom holder bracket 124 rotates back and forth, the opaque regions 138 alternately pass through the optical switches to provide absolute position feedback regarding the position of the phantom holder bracket 124. The outputs of the optical switches 134 are provided to the servo controller 132 and the patient simulator circuit 120.

The patient simulator circuit 120 utilizes the position feedback from one of the switches 134 to generate a simulated EKG signal. The simulated EKG signal is provided to the DAS 32 of the CT system 10, which uses the simulated EKG signal as a trigger signal to trigger image acquisition. Therefore, image acquisition is synchronized to movement of the phantom 50, just as image acquisition would be synchronized to movement of an actual human heart. In practice, the simulated EKG signal may simply be a signal having a simulated R-pulse.

Figure 10:
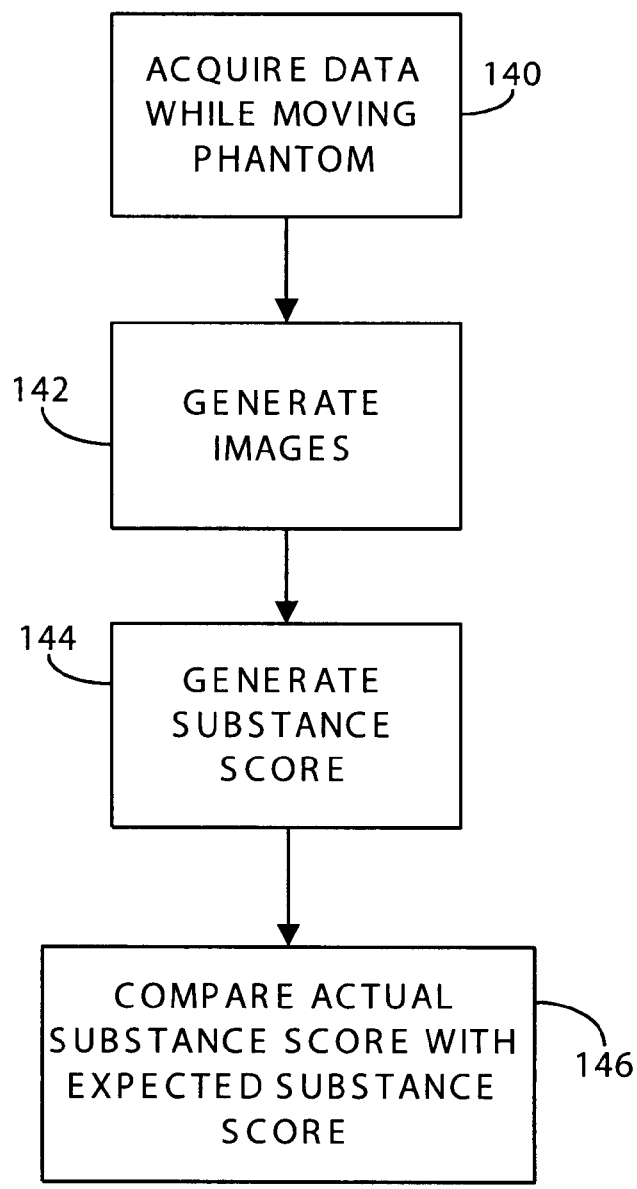
FIG. 10 is a flowchart showing the operation of the system of FIG. 8.
Figure 11:
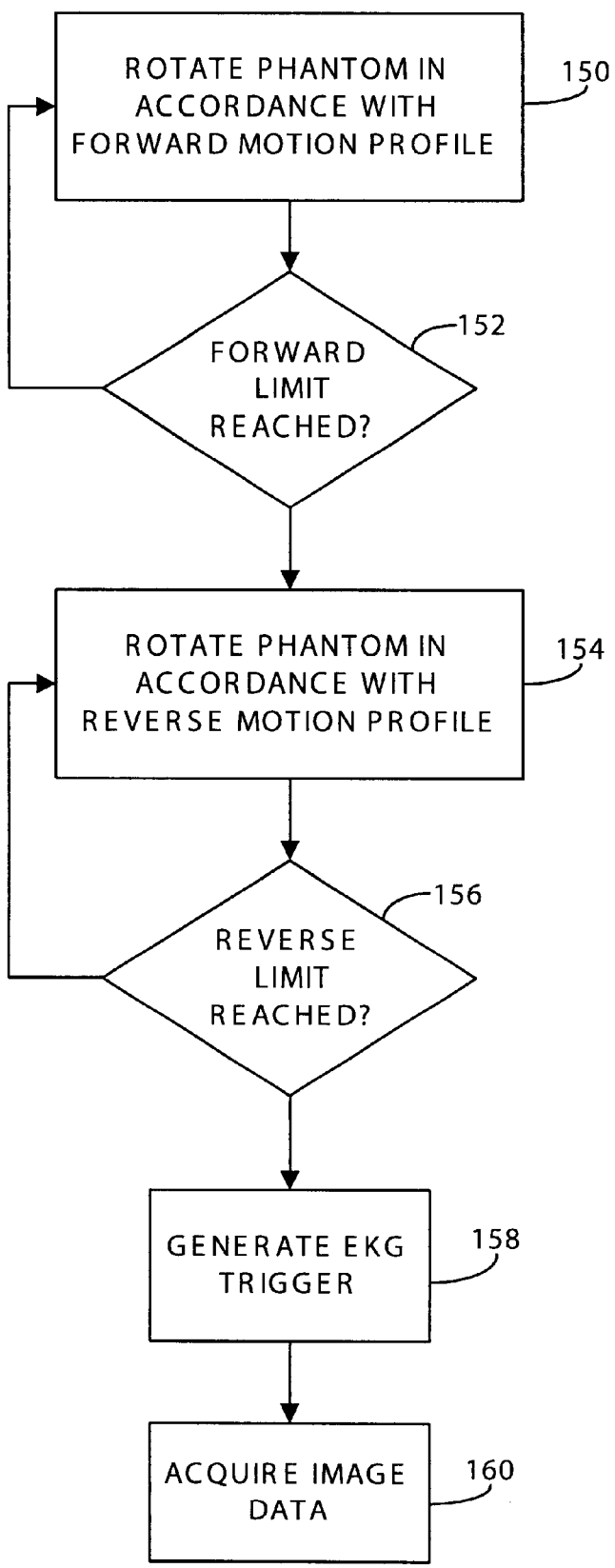
FIG. 11 is a flowchart showing one of the steps of FIG. 10 in greater detail.

Referring now also to FIG. 10, a flowchart showing the operation of the system of FIG. 8 is shown. At step 140, the phantom holder assembly 115 moves the phantom 50 as the CT system 10 acquires data from the phantom 50. Step 140 is shown in greater detail in FIG. 11. At step 150, the phantom holder assembly 115 rotates the phantom 50 in the forward direction in accordance with a forward motion profile. The volume and shape of the phantom 50 do not change during movement of the phantom 50. Forward movement continues until a forward limit is reached (as detected by the optical switch 134) at step 152. Thereafter, at step 154, the phantom holder assembly 115 rotates the phantom 50 in the reverse direction in accordance with a reverse motion profile. Reverse movement continues until a reverse limit is reached (as detected by the optical switch 134) at step 156. When the reverse limit is reached, the signal from the optical switch 134 causes the patient simulator circuit 120 to produce a simulated R-pulse in the simulated EKG signal at step 158. The R-pulse is received as part of the simulated EKG signal by the imaging system 10. The imaging system 10 is triggered by the R-pulse and in response acquires additional image data at step 160. Although only a single data acquisition step is shown in FIG. 11, it may be noted that multiple data acquisition steps may be performed concurrently with the other steps of FIG. 11, such that each simulated R-pulse is used to trigger a series of data acquisition steps. Also, it may be noted that the process of FIG. 11 is repeatedly performed until a complete scan has been performed.

Figure 12:
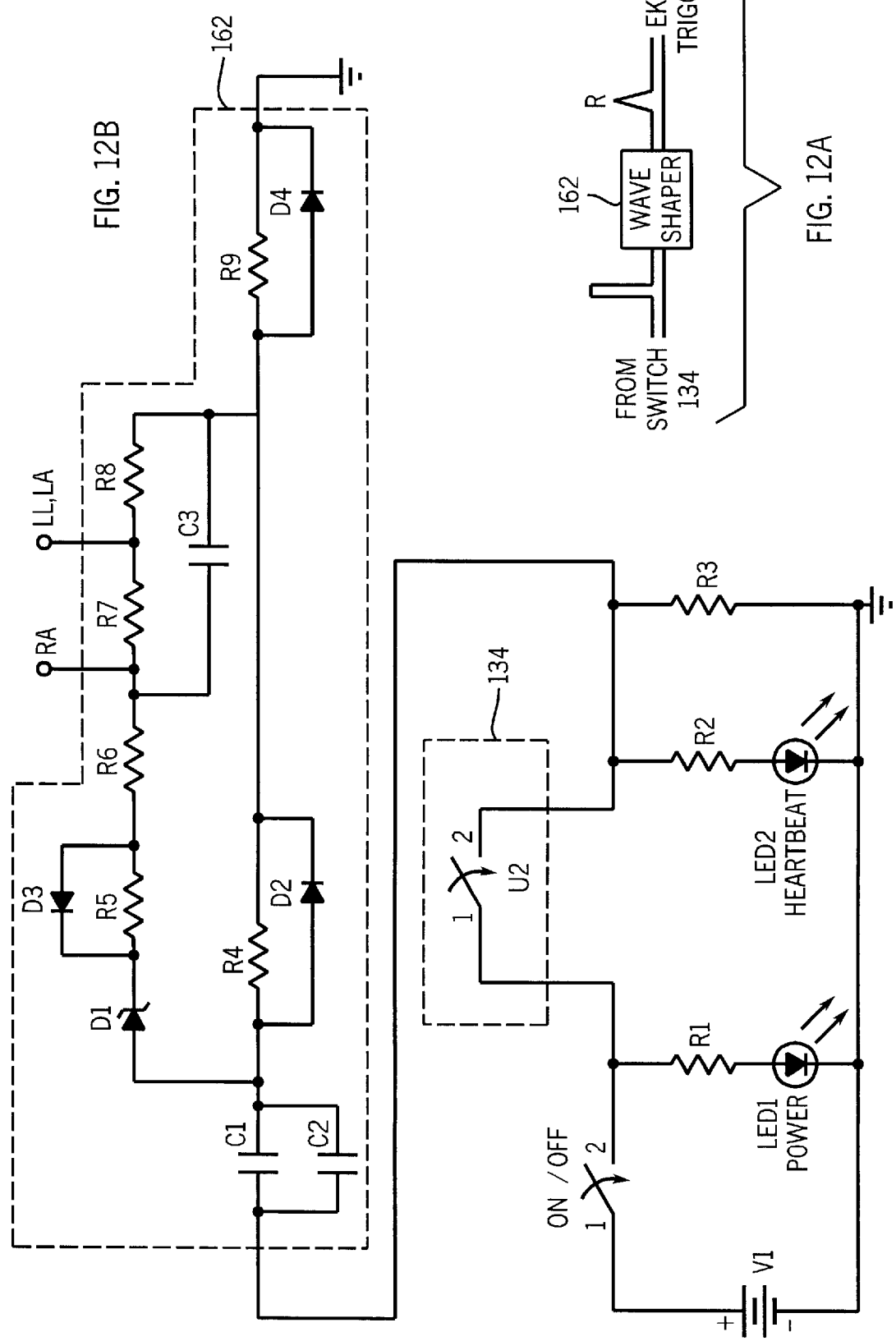
FIG. 12A is a block diagram of a patient simulator circuit of FIG. 8.

FIG. 12A shows a block diagram of the patient simulator circuit 120 of FIG. 8 in greater detail. When the phantom 50 reaches its motion limit, the switch 134 temporarily closes, applying a positive voltage pulse to wave shaper circuitry 162. The wave shaper circuitry 162 shapes the voltage pulse so as to resemble an R-pulse suitable for triggering the imaging system 10. It is not necessary that the simulated EKG signal produced by the patient simulator circuit 120 comprise any other pulses other than the R-pulses used to trigger the imaging system 10. FIG. 12B illustrates an exemplary implementation of the circuit of FIG. 12A. The component values for the components of the circuit of FIG. 10B are provided in the table below:

| Part | Value | Part | Value | Part | Value |
|---|---|---|---|---|---|
| R1 | 2.94 KΩ | C1 | 3.0 µF | V1 | 9 V |
| R2 | 2.94 KΩ | C2 | 2.0 µF | LED1 | CR022 |
| R3 | 2.94 KΩ | C3 | 1.0 µF | | DS1 |
| R4 | 15 KΩ | D1 | D1N4733 | LED2 | CR022 |
| R5 | 40.2 KΩ | D2 | D1N4148 | | DS2 |
| R6 | 10 KΩ | D3 | D1N4148 | | |
| R7 | 22.6 Ω | D4 | D1N4148 | | |
| R8 | 2.94 KΩ | | | | |
| R9 | 15 KΩ | | | | |

Of course, the patient simulator circuit could also be implemented in other ways.

Referring back to FIG. 10, once the data is acquired using the CT system 10, the data is then converted to images of the phantom 50 at step 142. The converted data is then used to generate an actual substance score for the phantom 50 at step 144 in accordance with the substance scoring algorithm that is being evaluated. The scoring algorithm is stored in the computer 36. In the preferred embodiment, in which the phantom 50 simulates a human heart and comprises volumes 70 that simulate calcium present in the human heart, the substance scoring system is a calcium scoring system and provides an output which expresses a quantity and a concentration of calcium present in the phantom 50 or human heart. Therefore, the actual substance score generated for the phantom 50 expresses a quantity and a concentration of simulated calcium present in the phantom 50. At step 146, the actual substance score is then compared to an expected substance score for the phantom to evaluate the scoring algorithm.

Figure 13:
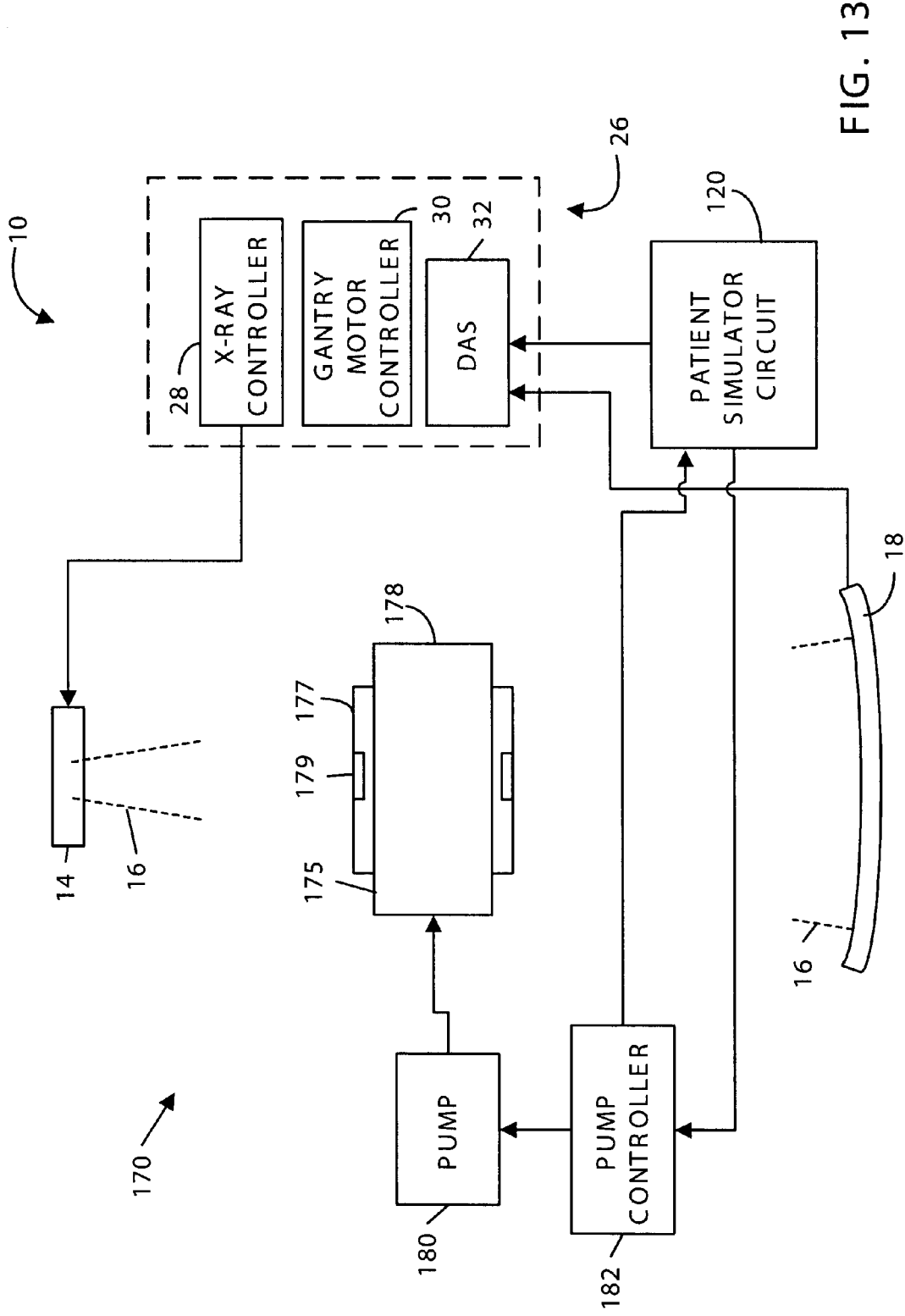
FIG. 13 is a block diagram of a system that incorporates an alternative phantom.

In another embodiment and referring now to FIG. 13, FIG. 13 is a block diagram of an alternative calcium scoring evaluation system 170 that incorporates an alternative pump-based phantom 175. The phantom 175 is hollow and is constructed of an expandable material. The phantom 175 includes a jacket 177 which surrounds an inner expandable pouch or balloon 178. The jacket 177 is used to mount volumes 179 of material that simulate calcium in the same manner as discussed above in connection with the volumes 70 of the phantom 50. The phantom 175 is preferably manufactured for durability and repeatable results across similarly-constructed phantoms. The system also includes a pump 180 and a pump controller 182 instead of the motor 130 and the motor servo controller 132 of FIG. 8. The pump controller 182 controls the pump 180, which is used to control fluid inflow and outflow from the phantom 175.

Figure 14:
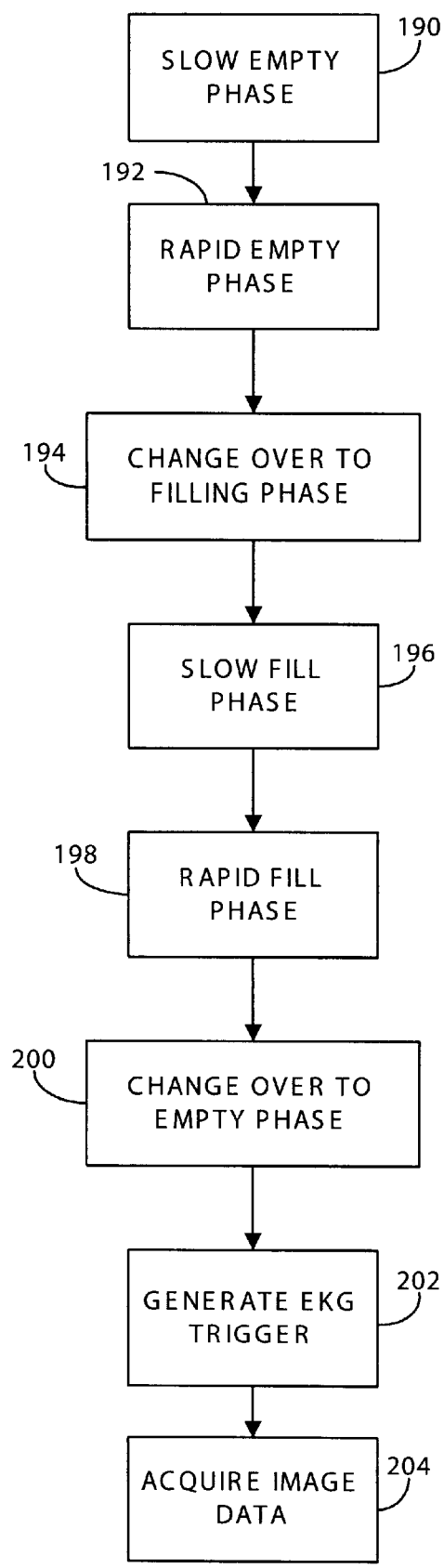
FIG. 14 is a flowchart showing one of the steps of FIG. 10 in greater detail in for the evaluation system of FIG. 13.

The operation of the system 170 is the same as the operation of the system 110 as described above in connection with FIG. 10, except that step 140 (described in connection with FIG. 11) is implemented differently. FIG. 14 shows the implementation of step 140 in the context of the evaluation system 170. The pump controller 182 controls the pump 180 such that motion of the phantom 175 mimics cardiac motion. The pumping rate is based upon a motion profile calculated based on volume change at different phases of the heart. Thus, as shown in FIG. 14, the pumping comprises a slow empty phase (e.g., for a duration of 100 ms) at step 190, followed by a rapid empty phase (e.g., for a duration of 150 ms) at step 192, followed by a change over to filling phase (e.g., for a duration of 50 ms) at step 194, followed by a rapid filling phase (e.g., for a duration of 100 ms) at step 196, followed by a slow filling phase (e.g., for a duration of 500 ms) at step 198, followed by a change over to empty phase (e.g., for a duration of 100 ms) at step 200. The process then includes an EKG trigger step 202 and an image data acquisition step 204, which are the same as described above in connection with steps 158 and 160, except that the triggering step is performed by the pump controller 182. Alternatively, appropriate feedback sensors may be provided on the phantom 175 analogous to the switches 134.

When fluid is pumped into and emptied from the phantom 175, the volume of the phantom 175 changes and the phantom 175 changes shape. The pumping and emptying steps cause the outer surface of the phantom 175 to move due to expansion and contraction of the phantom 175 when the fluid enters and exits the phantom 175. Therefore, since the volumes 179 are mounted near the outer surface of the phantom 175, the volumes 179 also move.

Preferably, the motion profile for the phantom 175 is generated based on an EKG signal from a human patient. The duration and flow rate during each phase is determined based on the duration and slopes of the various deflections in the EKG signals (P-wave, QRS-wave and T-wave), respectively. Therefore, the velocity at which fluid enters the phantom 175 and exits the phantom is controlled during the pumping and emptying steps 190–200 such that the phantom 175 is provided with a time-varying motion profile that simulates a motion profile of the human heart during pumping of the human heart. To evaluate the substance scoring system for a plurality of different heart pumping profiles, the pumping and emptying steps may be repeated for multiple different motion profiles generated based on multiple different EKG signals obtained from multiple different human patients.

Although embodiments of phantoms 50 and 175 are shown herein relative to a CT imaging system and for use with a calcium scoring system using a scoring algorithm, phantoms 50 and 175 can also be used with other imaging systems, other calcium scoring systems and other scoring algorithms. Furthermore, phantoms 50 and 175 are not limited to use with calcium scoring systems but can be used to quantify other substances besides calcium. Alternative embodiments of phantoms 50 and 175 also can be used to evaluate patient regions of interest other than the heart.

While the invention has been described in terms of various specific embodiments, those skilled in the art will recognize that the invention can be practiced with modification within the spirit and scope of the claims.

What is claimed is:

1. A method of evaluating a substance scoring system, comprising:
   acquiring data from a phantom using an imaging system, said phantom simulating at least a portion of a human organ;
   moving at least a portion of said phantom during said acquiring step, including providing said phantom with a motion profile that simulates a motion profile of the human organ; and
   generating an actual substance score for said phantom based on said data acquired using said imaging system.

2. A method according to claim 1, wherein said substance scoring system is a calcium scoring system that provides a score that is indicative of a quantity and concentration of calcium in the human organ, and wherein said imaging system is a computed tomography imaging system.

3. A method according to claim 1,
   wherein the substance scoring system is a calcium scoring system and provides an output which expresses a quantity and a concentration of calcium present in the human organ;
   wherein the phantom simulates the human organ and comprises volumes of material that simulate calcium;
   wherein said actual substance score expresses a quantity and a concentration of simulated calcium present in said phantom.

4. A method according to claim 3, wherein said phantom comprises a core and a plurality of volumes embedded in said core, each of said plurality of volumes having an imaging number that simulates calcium, with different ones of said plurality of volumes having different imaging numbers that simulate different concentrations of calcium.

5. A method according to claim 4,
   wherein said phantom is mounted to a phantom holder;
   wherein said moving step is performed by said phantom holder; and
   wherein said phantom maintains a constant shape during said moving step.

6. A method according to claim 3,
   wherein the human organ is a human heart;
   wherein said moving step comprises causing a volume of said phantom to change;
   wherein said portion of said phantom is an outer surface of said phantom, said outer surface of said phantom moving in response to changes in said volume of said phantom;
   wherein said volume of said phantom is controlled such that said phantom is provided with a time-varying motion profile that simulates a motion profile of a human heart during pumping of the human heart.

7. A method according to claim 3,
   wherein the human organ is a human heart;
   wherein said moving step comprises causing said phantom to change shape; and
   wherein said portion of said phantom is an outer surface of said phantom, said outer surface of said phantom moving when said phantom changes shape.

8. A method according to claim 7, wherein said moving step comprises
   pumping fluid into said phantom; and
   emptying said fluid from said phantom; and
   wherein said pumping and emptying steps cause said outer surface of said phantom to move due to expansion and contraction of said phantom when said fluid enters and exits said phantom.

9. A method according to claim 8, wherein a velocity at which fluid enters said phantom and exits said phantom is controlled during said pumping and emptying steps such that said phantom is provided with a time-varying motion profile that simulates a motion profile of the human heart during pumping of the human heart.

10. A method according to claim 1, further comprising
    generating a simulated EKG signal based on actual movement of said phantom; and
    providing said simulated EKG signal to said imaging system and triggering said acquiring step at said imaging system based on said simulated EKG signal.

11. A method according to claim 1, wherein the human organ is a human heart, and wherein said motion profile for said phantom is generated based on an EKG signal from a human patient.

12. A method according to claim 11, further comprising evaluating said substance scoring system for a plurality of different heart pumping profiles, including repeating said moving step for a plurality of different motion profiles generated based on a plurality of different EKG signals obtained from a plurality of different human patients.

13. A method according to claim 1, wherein said phantom comprises a core and a plurality of volumes embedded in said core, each of said plurality of volumes having an imaging number that simulates the substance, with different ones of said plurality of volumes having different imaging numbers that simulate different concentrations of the substance.

14. A system comprising:
    (A) a phantom including
        (1) a core, and
        (2) a plurality of volumes embedded in said core, each of said plurality of volumes having an imaging number that simulates a substance of interest, with different ones of said plurality of volumes having different imaging numbers that simulate different concentrations of the substance;
    (B) a movable phantom holder, said phantom being mounted to said phantom holder, and said phantom holder causing said phantom to move; and
    (C) an imaging system, said imaging system generating an actual substance score, said actual substance score expressing a quantity and a concentration of the simulated substance present in said phantom.

15. A system according to claim 14,
wherein said phantom further comprises a ring surrounding said core; and
wherein said core has an imaging number representative of heart muscle density and said ring has an imaging number representative of density of tissue surrounding a heart.

16. A system according to claim 14, wherein said different imaging numbers include numbers in each of the following ranges: zero to 129 Hounsfield units, 130 to 199 Hounsfield units, 200 to 299 Hounsfield units, 300 to 399 Hounsfield units, and greater than or equal to 400 Hounsfield units.

17. A system according to claim 14,
wherein the substance scoring system is a calcium scoring system and provides an output which expresses a quantity and a concentration of calcium present in a human heart;
wherein the phantom simulates the human heart and comprises a volumes of material that simulates calcium.

18. A method of evaluating a calcium scoring system, comprising:
analyzing an EKG signal obtained from a human heart of a human patient;
generating a motion profile for a phantom based on said EKG signal, said phantom comprising a hollow structure formed of an expandable material, said phantom simulating a human heart;
pumping a fluid into said phantom and emptying said fluid from said phantom, said fluid being pumped and emptied such that said phantom is provided with a motion profile that simulates said motion profile of the human heart during production of said EKG signal;
acquiring data from a phantom using a computed tomography imaging system;
generating an actual substance score for said phantom based on said data acquired using said imaging system.

19. A method according to claim 18, further comprising evaluating said substance scoring system for a plurality of different heart pumping profiles, including
generating a plurality of additional motion profiles for a plurality of additional EKG signals obtained from a plurality of additional human patients;
repeating said pumping and emptying steps for said plurality of additional EKG signals; and
comparing said actual substance score for said phantom to an expected substance score for said phantom for said EKG signal and for said plurality of additional EKG signals.

20. A method according to claim 18, further comprising
generating a simulated EKG signal based on actual movement of said phantom; and
providing said simulated EKG signal to said imaging system and triggering said acquiring step at said imaging system based on said simulated EKG signal.

21. A system comprising:
means for acquiring data from a phantom using an imaging system, said phantom simulating at least a portion of a human organ;
means for moving at least a portion of said phantom during said acquiring step, including providing said phantom with a motion profile that simulates a motion profile of the human organ; and
means for generating an actual substance score for said phantom based on said data acquired using said imaging system.

* * * * *

UNITED STATES PATENT AND TRADEMARK OFFICE
CERTIFICATE OF CORRECTION

| | | |
|---|---|---|
| PATENT NO. | : 6,697,451 B1 | |
| DATED | : February 24, 2004 | |
| INVENTOR(S) | : Kishore C. Acharya, Marcela A. Gonzalez and Gary J. Walloch | |

It is certified that error appears in the above-identified patent and that said Letters Patent is hereby corrected as shown below:

Column 9,
Line 31, delete "." and insert -- ; --.
Line 32, insert, -- wherein the substance scoring system provides an output which expresses a quantity and a concentration of a substance present in the human organ;
    wherein the phantom simulates the human organ and comprises volumes of material that simulate the substance;
    wherein said actual substance score expresses a quantity and concentration of the simulated substance present in said phantom. --
Line 37, delete "according to claim 1," and insert -- of evaluating a substance scoring system, comprising: --
Line 38, insert -- acquiring data from a phantom using an imaging system, said phantom simulating at least a portion of a human organ;
    moving at least a portion of said phantom during said acquiring step, including providing said phantom with a motion profile that simulates a motion profile of the human organ; and
    generating an actual substance score for said phantom based on said data acquired using said imaging system; --

Column 10,
Line 28, delete "according to claim 1, further" and insert -- of evaluating a substance scoring system, --
Line 29, insert -- acquiring data from a phantom using an imaging system, said phantom simulating at least a portion of a human organ;
    moving at least a portion of said phantom during said acquiring step, including providing said phantom with a motion profile that simulates a motion profile of the human organ;
    generating an actual substance score for said phantom based on said data acquired using said imaging system; --
Line 34, delete "according to claim 1,"
Line 34, insert after "method" -- of evaluating a substance scoring system, comprising:
    acquiring data from a phantom using an imaging system, said phantom simulating at least a portion of a human organ;
    moving at least a portion of said phantom during said acquiring step, including providing said-phantom with a motion profile that simulates a motion profile of the human organ; and
    generating an actual substance score for said phantom based on said data acquired using said imaging system; --
Line 44, delete "according to claim 1,"

UNITED STATES PATENT AND TRADEMARK OFFICE
CERTIFICATE OF CORRECTION

PATENT NO. : 6,697,451 B1
DATED : February 24, 2004
INVENTOR(S) : Kishore C. Acharya, Marcela A. Gonzalez and Gary J. Walloch It is certified that error appears in the above-identified patent and that said Letters Patent is hereby corrected as shown below:

Column 10 cont'd.,
Line 44, insert after "method" -- of evaluating a substance scoring system, comprising:
 acquiring data from a phantom using an imaging system, said phantom simulating at least a portion of a human organ;
 moving at least a portion of said phantom during said acquiring step, including providing said phantom with a motion profile that simulates a motion profile of the human organ; and
 generating an actual substance score for said phantom based on said data acquired using said imaging system; --

Column 11,
Line 19, delete "a"
Line 36, delete the first "a" and replace with -- said --

Column 12,
Line 24, insert after "system" -- for evaluating a substance scoring system --
Line 25, delete "using an imaging system"
Line 33, delete "acquired using said imaging system"
Line 33, insert after "data" -- ; --
Line 35, insert -- wherein the substance scoring system provides an output which expresses a quantity and a concentration of a substance present in the human organ;
 wherein the phantom simulates the human organ and comprises volumes of material that simulate the substance;
 wherein said actual substance score expresses a quantity and concentration of the simulated substance present in said phantom. --

Signed and Sealed this

Seventeenth Day of August, 2004

JON W. DUDAS
*Acting Director of the United States Patent and Trademark Office*